(12) United States Patent
Buchholz et al.

(10) Patent No.: US 6,921,535 B2
(45) Date of Patent: Jul. 26, 2005

(54) ATTENUATED BOVINE RESPIRATORY SYNCYTIAL VIRUS

(75) Inventors: Ursula J. Buchholz, Bethesda, MD (US); Ulrike Schmidt, Goch (DE)

(73) Assignee: Akzo Nobel N.V., Arnhem (NL)

( * ) Notice: Subject to any disclaimer, the term of this patent is extended or adjusted under 35 U.S.C. 154(b) by 0 days.

(21) Appl. No.: 10/312,232

(22) PCT Filed: May 2, 2001

(86) PCT No.: PCT/EP01/05085

§ 371 (c)(1), (2), (4) Date: Dec. 23, 2002

(87) PCT Pub. No.: WO02/02752

PCT Pub. Date: Jan. 10, 2002

(65) Prior Publication Data

US 2004/0037850 A1 Feb. 26, 2004

(30) Foreign Application Priority Data

Jun. 23, 2000 (EP) .............................................. 00202183

(51) Int. Cl.$^7$ ............................................. A61K 39/155
(52) U.S. Cl. ................................ 424/211.1; 424/204.1; 424/205.1; 424/199.1; 435/6; 435/320.1
(58) Field of Search .......................... 424/211.1, 204.1, 424/205.1, 199.1; 435/6, 320.1

(56) References Cited

U.S. PATENT DOCUMENTS 6,033,886 A * 3/2000 Conzelmann ............ 424/205.1
6,699,476 B1 * 3/2004 Collins et al. ........... 424/199.1

FOREIGN PATENT DOCUMENTS

| EP | 0702085 A1 | * 12/1996 |
| EP | 0 974 660 A | 1/2000 |
| WO | 98 02530 A | 1/1998 |

OTHER PUBLICATIONS

Whitehead S. S. et al: "Recombinant respiratory syncytial virus bearing a deletion of either the NS2 or SH gene is attenuated in chimpanzees."; Journal of Virology, vol. 73, No. 4, Apr. 1999; pp. 3438–3442.

Karger A. et al: "Recombinant bovine respiratory syncytial virus with deletions of the G or SH genes: G and F proteins bind heparin"; Journal of General Virology, vol. 82, No. 3, Mar. 2001; pp. 631–640.

Karron R. A. et al: "Respiratory syncytial virus (RSV) SH and G proteins are not essential for viral replication in vitro: Clinical evaluation and molecular characterization of a cold–passaged, attenuated RSV subgroup B mutant"; Proceedings of the National Academy of Sciences of the United States, vol. 94, No. 25, Dec. 9, 1997, pp. 13961–13966.

Buchholz U. J. et al: "Chimeric bovine respiratory syncytial virus with glycoprotein gene substitutions from human respiratory syncytial virus (HRSV): Effects on host range and evaluation as a live–attenuated HRSV vaccine." Journal of Virology, vol. 74, No. 3, Feb. 2000, pp. 1187–1199.

Dudas R. A. et al: "Respiratory syncytial virus vaccines", Clinical Microbiology Reviews, vol. 11, No 3, Jul. 1998, pp. 430–439.

Whitehead S.S. et al: "Replacement of the F and G proteins of respiratory syncytial virus (RSV) subgroup A with thos of subgroup B generates chimeric live attenuated RSV subgroup B vaccine candidates", Journal of Virology, vol. 73, No 12, Dec. 1999, pp. 9773–9780.

* cited by examiner

Primary Examiner—Ali R. Salimi
(74) Attorney, Agent, or Firm—Mark W. Milstead

(57) ABSTRACT

The present invention relates i.a. to Bovine Respiratory Syncytial Viruses that are not capable of expressing a functional SH-protein and/or G-protein due to a mutation in the genes encoding the said proteins. Furthermore, the invention relates to vaccines based upon such Bovine Respiratory Syncytial Viruses and to methods for the preparation of such vaccines. Also the invention relates to diagnostic test kits for discriminating wild-type Bovine Respiratory Syncytial Viruses from Bovine Respiratory Syncytial Viruses according to the invention and to methods for the discrimination between those viruses.

6 Claims, 6 Drawing Sheets

Multicycle growth of rBRSV, rBRSVΔSH, rBRSVΔG, and rBRSVΔSHG in MDBK cells

Fig. 6

Group I
mock-immunization
and challenge calf 26
calf 36
calf 37

Group II
rBRSVΔG-immunization
and challenge calf 28
calf 77
calf 41
calf 76

Group III
rBRSV-immunization and
challenge calf 29
calf
calf
calf

ATTENUATED BOVINE RESPIRATORY SYNCYTIAL VIRUS

BACKGROUND OF THE INVENTION

Field of the Invention

The present invention relates to attenuated Bovine Respiratory Syncytial virus (BRSV), vaccines based thereon, methods for the preparation of such vaccines, methods for the discrimination between field-infected mammals and vaccinated mammals, and to diagnostic tests kits.

Bovine Respiratory Syncytial virus is a member of the family paramyxoviridae, and belongs to the genus of the Pneumoviruses. Paramyxoviridae belonging to this genus are human RSV, bovine RSV, ovine RSV, caprine RSV and pneumonia virus of mice. RSV are a member of the order Mononegavirales, i.e. the virus is a non-segmented negative strand RNA virus. The overall genomic organization of the non-segmented negative stranded RNA of the viruses belonging to the genus Pneumoviruses is comparable. The RNA consists of 10 genes, encoding eleven proteins, and has a length of about 15.2 kilobases. The RSV-proteins include two non-structural proteins (NS1 and NS2), four RNA-associated proteins, the nucleoprotein N, phosphoprotein P, the large, catalytic subunit L of the RNA-polymerase, a transcription elongation factor encoded by the first of two overlapping open reading frames of the M2 gene, and three envelope-associated proteins; the fusion protein F, the attachment protein G and the small hydrophobic protein SH. One characteristic shared by all pneumoviruses is the fact that they cause infections of the upper and (in most cases) lower respiratory tract. The human RSV has a world wide distribution and has been found to be the major pediatric viral respiratory tract pathogen. Infection of bovine species with BRSV is highly comparable to HRSV infection in many respects, i.a. in the sense that it mainly causes disease in young animals. (For a review, see Van der Poel et al.; J. Inf. 29: 215–228 (1994)). Although re-infections occur frequently in both species, in cattle they usually do not cause clinical signs (Kimman and Westenbrink, Archives of Virology 1990, 112, 1–25) which suggests that a natural infection protects against clinical signs after reinfection. Mortality varies between 1% and 30%, depending on various parameters, such as virulence of the infecting strain, climate, level of animal care and occurrence of secondary infections. (Stott et al., J. Hygiene 85: 251–261 (1980), Verhoeff, et al. Vet. Rec. 115: 488–492 (1984)). The morbidity is very high (Baker et al., Am. J. Vet. Res. 46: 891–892 (1985), Baker et al., Vet. Clin. N. Am.: Food Animal Practice 1: 259–275 (1985)). Mortality due to BRSV-infection including those cases in which BRSV infection is followed by infection with other pathogens is very high, and thus the economical losses world-wide are consequently very high.

It is clear, that efficacious and reliable vaccines for both the protection against human RSV and bovine RSV are highly wanted, but vaccine development has been hampered because it is not known how a protective immune response can be induced without causing disease. First attempts to vaccinate children with formalin-inactivated vaccines led to enhanced disease after natural infection, which suggests that vaccination may even be harmful (Anderson et al., Journal of Infectious Diseases 1995, 171, 1–7). It is known, however, that antibodies against two major surface proteins, F (a fusion protein) and G (an attachment protein), play a key role in protection (Kimman and Westenbrink, Archives of Virology 1990, 112, 1–25). However, so far vaccines based on the F- or G-protein, i.e. subunit vaccines, have not been disclosed in the literature.

One way to mimic the natural infection, c.q. to efficiently trigger the host's defense mechanism is to develop a live attenuated vaccine. Such a vaccine mimics the natural triggering of the immune system, whereas due to its attenuated characteristics, it does not induce the severe clinical signs caused by the wild-type virus. The attenuated character is usually obtained by mutating a gene that on the one hand plays a role in virulence, but on the other hand is not essential for viral infection and replication, and moreover plays no role in the induction of immunity.

Live attenuated vaccines must, as closely as possible, mimic the native RSV as far as their infection behavior is concerned. One of the main characteristics of native Respiratory Syncytial Virus is that shortly after infection it causes formation of large syncytia. Formation of these syncytia, the result of large scale cell fusion, requires the presence of the F-, the G- and the SH-protein. (Heminway, B. R. et al., Virology 200: 801–805 (1994). Expression of individual F-, SH- or G-proteins does not result in syncytia-formation. Co-expression of both the F- and SH-gene, or of both the F- and G-gene gives only very low level cell-fusion (Pastey, M. K. and Samal, S. K., J. Gen. Virol. 78: 1885–1889 (1997)). Therefore, it could be assumed that an attenuated virus suitable for use as a vaccine closely mimicking the natural infection should in principle express the proteins F, G and SH. Deletion of the gene encoding either protein G or SH results in lack of significant syncytium formation as mentioned above. Moreover, deletion of G, known to be a significant immunogen would be undesirable anyway for a vaccine virus. Therefore, if an attenuated vaccine virus is needed, a mutant RSV lacking either the SH-gene or the G-gene is not a logic choice. For these reasons, it is clear that a mutant virus that lacks even both the G-protein and the SH-protein would be the most unattractive choice for use in vaccines, because:

1) it does not form syncytia, and thus lacks one of the most characterizing features of native RSV
2) it lacks one of the two immunodominant antigens.

Karron described a human RSV lacking both the SH-gene and the G-gene (Karron et al., Proc. Natl. Acad. Sci. 94: 13961–13966 (1997)). It was tested in patients for its suitability as a vaccine virus. The virus was however not capable of inducing an immune response in patients. As could be predicted on the basis of the arguments given above, the fact that it lacks both these genes, makes the virus over-attenuated and therefore unsuitable for vaccination purposes.

BRIEF SUMMARY OF THE INVENTION

It was now surprisingly found that bovine RSV having a deletion in the G-gene or in the SH- and G-gene is still capable of inducing protective immunity in animals. The present invention therefore encompasses mutants of BRSV with a mutation in the G-gene, and, optionally, in the SH gene as well.

DETAILED DESCRIPTION OF THE INVENTION

Thus, one embodiment of the invention provides Bovine Respiratory Syncytial Virus not capable to express a functional SH-protein and G-protein due to a mutation in the genes encoding these proteins.

The mutation can lead to the expression of a non-functional SH-protein and G-protein protein or, depending on the nature of the mutation, no SH-protein and G-protein at all. A non-functional SH-protein or G-protein is considered to be a protein that lacks some or all of the characteristics of the SH-protein or G-protein as expressed in a wild-type virus, and/or is expressed at a level, insufficient to obtain wild-type levels of SH-protein or G-protein. A particular form of a BRSV mutant according to the invention is e.g. a mutant that in a standard ELISA test is not reactive with antibodies raised against purified SH-protein nor against purified G-protein.

A mutation is understood to be a change of the genetic information in the above-mentioned SH- and G-gene in comparison to the genetic information present in this gene in the parent BRSV.

A gene is understood to comprise the coding region that encodes a (glyco)protein as well as those elements that play a role in the transcription and translation of the gene, such as polymerase binding sites, ribosome binding sites, enhancers and the like.

The mutation is a nucleic acid substitution, deletion, insertion or inversion, or a combination thereof.

In principle, mutants according to the invention can be selected in vivo from animals in the field, by screening for viruses not capable to express a functional SH-protein and G-protein. Another possibility is to screen for in vitro grown viruses not capable to express a functional SH-protein and G-protein after serial passages of wild-type virus over suitable host cells. Such methods are well-known in the art and belong to the classical ways of making attenuated viruses. Such methods however are time-consuming.

Mutations can more easily and deliberately be introduced by means of standard recombinant DNA technology. Standard recombinant DNA techniques such as making cDNA, cloning of cDNA in a plasmid, digestion of the gene with a restriction enzyme, followed by endonuclease treatment, re-ligation and homologous recombination in the host strain, are all known in the art and described i.a. in Maniatis/Sambrook (Sambrook, J. et al. Molecular cloning: a laboratory manual. ISBN 0-87969-309-6). Site-directed mutations can e.g. be made by means of in vitro site directed mutagenesis using the Transformer® kit sold by Clontech. The sequences of the SH- and G-gene to be mutated are also known in the art: the nucleotide sequence of the bovine RSV SH-gene has been published by Samal, S. K., and M. Zamora (J. Gen. Virol. 72: 1715–1720 (1991) and the nucleotide sequence of the bovine RSV G-gene has been published by Lerch, R. A., K. Anderson, and G. Wertz. (J. Virol. 64: 5559–5569 (1990)). The full genome of a typical BRSV strain (strain ATue51908, as deposited in the GenBank database under accession no. AF092942), has been sequenced by Buchholz, U. J., S. Finke, and K.-K. Conzelmann. (J. Virol. 73: 251–259 (1999)). The SH-gene is located between nucleotide 4186 and 4651 at the genome of BRSV strain ATue51908, and the coding sequence is located between nucleotide 4268 and 4513. The G-gene is located between nucleotide 4690 and 5529 at the genome of BRSV strain ATue51908, and the coding sequence is located between nucleotide 4705 and 5478.

Theoretically, nucleic acid mutations such as substitutions, inversions and even insertions may lead to reversion to the native nucleic acid sequence. This may be due to repeated substitution, re-inversion or loss of the inserted sequence. Therefore, the safest mutation is a deletion mutation: a fragment that has been deleted can not be regained. Thus, in a preferred embodiment, the invention relates to Bovine Respiratory Syncytial virus, that has as a characteristic feature that the mutation in the SH- or G-gene is a deletion mutation. The size of the deletion may vary from small, e.g. one nucleotide as a result of which the downstream reading frame is disturbed, to a large deletion encompassing the whole SH- or G-gene.

Methods for the preparation of non-segmented negative stranded RNA viruses have been described in EP 0702085.

Methods for the preparation of recombinant BRSV, starting from plasmids harboring the various BRSV-genes as e.g. cDNA copies have been published i.a. by Collins et al., in Proc. Natl. Acad. Sci 92: 11563–11567 (1995). Mutations in the genes encoded by those plasmids can easily be made as discussed above.

BRVS mutants according to the present invention are very suitable as carriers for heterologous RNA sequences. Therefore, a more preferred form of this embodiment relates to BRSV mutants comprising a heterologous RNA sequence. This heterologous RNA can be inserted in a region outside the SH- or G-gene, provided that the viability of the virus is not destroyed. Suitable regions are e.g. intergenic regions or genes that are not essential to the virus.

More efficiently however, the heterologous RNA is inserted in a region that was deleted from the SH- or G-gene. Or even more efficiently, it can also be inserted somewhere in the full length SH- or G-gene leading to the production of a non-functional SH-protein or G-protein or no SH-protein or G-protein at all. A heterologous RNA sequence is a sequence that originates from a source, other than the parental BRSV strain. It may be derived from the DNA of another organism or may be synthetically made. The heterologous RNA sequence may e.g. be a sequence that interferes with transcription or translation of SH or G. Such sequences may be transcription termination signals or polyadenylation sites but they may also contain translational stop-codons.

In an even more preferred form, the heterologous RNA sequence codes for a polypeptide. Therefore, in a more preferred form the invention relates to Bovine Respiratory Syncytial virus according to the invention carrying a heterologous gene, more preferably inserted in the SH-gene or the G-gene.

The heterologous RNA sequence may contain promotor sequences such that expression is under control of these sequences. These sequences may be the promotor sequences that are found to be linked to the heterologous gene coding for the polypeptide, in its native form, or it may be other promotor sequences suitable for expression in eukaryotic cells. It is obvious to those skilled in the art that the choice of a promotor extends to any eukaryotic, prokaryotic, viral or synthetically prepared promotor capable of directing gene transcription in cells infected by the BRSV mutant. Such promotors may be HRSV or BRSV promoters, but also promoters obtained from other RNA viruses are suitable.

In a still even more preferred form, the heterologous RNA sequence encodes an antigen of another mammalian pathogen, which is able to elicit a protective immune response, whereby the antigen is expressed by the BRSV mutant according to the invention upon replication in the host cell. This has the advantage that a mammal can be immunized against two or more diseases: BRSV and another disease In the most preferred form of this embodiment, the heterologous gene is selected from the group of cattle pathogens, consisting of Bovine Rotavirus, Bovine Viral Diarrhoea virus, Parainfluenza type 3 virus, Bovine Paramyxovirus, Bovine Herpesvirus, Foot and Mouth Disease virus and *Pasteurella haemolytica*. Those genes of the viruses and bacteria mentioned that are involved in triggering an immunological response are known in the art.

Furthermore, the heterologous RNA sequence may encode a cytokine. Several cytokines, e.g. interferons are known to play an important role as immune modulators. Thus it may be advantageous to include genetic information for this kind of molecule into said section.

A BRSV mutant according to the present invention, and in particular a live BRSV, optionally expressing one or more different heterologous polypeptides of specific pathogens can, due to its attenuated character, be used to vaccinate mammals. Vaccination with such a live vaccine or live vector vaccine is followed by replication of the BRSV mutant within the inoculated host, expressing in vivo the BRSV polypeptides, along with heterologous polypeptides if the encoding genes are inserted, but with the exception of functional SH and G. The polypeptides expressed in the inoculated host will then elicit an immune response against both BRSV and the specific pathogen. If the heterologous polypeptide derived from the specific pathogen can stimulate a protective immune response, then the mammal inoculated with the BRSV mutant according to the invention will be immune to subsequent infection by that pathogen as well as to infection by BRSV. Thus, a heterologous nucleic acid sequence incorporated into the insertion-region of the BRSV genome according to the invention may be expressed in vivo during several replication cycles, providing a solid, safe and long-lasting immunity to the pathogen from which it was derived.

Therefore, another embodiment of the invention relates to vaccines for the protection of mammals against Bovine Respiratory Syncytial virus infection. Such vaccines comprise a Bovine Respiratory Syncytial virus not capable of expressing a functional G-protein (and SH-protein) as a result of a mutation in the G-gene (and SH-gene) and a pharmaceutically acceptable carrier.

A BRSV mutant according to the invention containing and expressing one or more different heterologous polypeptides can serve as a multivalent vaccine.

For the preparation of a vaccine the BRSV mutant according to the present invention can be grown on susceptible cells, e.g. on a cell culture of bovine origin. The viruses thus grown can be harvested by collecting the tissue cell culture fluids and/or cells. The live vaccine may be prepared in the form of a suspension or may be lyophilized.

In addition to an immunogenically effective amount of the BRSV mutant according to the invention the vaccine comprises a pharmaceutically acceptable carrier or diluent. Examples of pharmaceutically acceptable carriers or diluents useful in the present invention include e.g. materials as simple as sterile water or physiological salt solution. Also, stabilizers such as SPGA, carbohydrates (e.g. sorbitol, mannitol, starch, sucrose, glucose, dextran), proteins such as albumin or casein, protein containing agents such as bovine serum or skimmed milk, plant hydrolysates and buffers (e.g. phosphate buffer).

Optionally, one or more compounds having adjuvant activity may be added to the vaccine. Suitable adjuvants are for example aluminum hydroxide, phosphate or oxide, oil-emulsions e.g. of Bayol F$^{(R)}$ or Marcol 52$^{(R)}$, saponins or vitamin-E solubilisate. These adjuvants have the advantage that they help to stimulate the immune system in a non-specific way, thus enhancing the immune response to the vaccine.

Thus in a preferred form of this embodiment, the vaccine comprises an adjuvant.

The useful effective amount to be administered will vary depending on the age and weight of the animal, the mode of administration and type of pathogen against which vaccination is sought. Nevertheless, since the live attenuated viruses according to the invention are self-propagating, the amount of virus initially administered is not critical. A suitable dosage can be for example about $10.^{3.0}$–$10.^{7.0}$ pfu/mammal.

For administration to mammals, the BRSV mutant according to the invention can be given inter alia intranasally, intradermally, subcutaneously or intramuscularly.

There are several ways to store both inactivated and live organisms. Storage in a refrigerator is e.g. a well-known method. Also often used is storage at −70° C. Viruses can also be kept in liquid nitrogen. Freeze-drying is another way of conservation. Freeze-dried viruses can be stored and kept viable for many years. Freeze-drying can be done according to all well-known standard freeze-drying procedures. Optional beneficial additives, such as e.g. skimmed milk, trehalose, gelatin or bovine serum albumin can be added in the freeze-drying process. Therefore, in a more preferred embodiment, the vaccine according to the present invention is in a freeze-dried form.

Another embodiment of the present invention relates to methods for the preparation of a vaccine according to the invention. In a simple form, such methods comprise admixing an attenuated Bovine Respiratory Syncytial virus according to the invention and a pharmaceutically acceptable carrier or diluent. In more complex forms, such methods may comprise admixing adjuvants, freeze-drying and other preparations known in the art.

A generally acknowledged problem in the field of vaccination is the following: the presence of antibodies against a certain pathogen in the serum of a host mammal indicates that the host has been infected with the pathogen, either in a virulent or attenuated form. In the case of BRSV this means that large amounts of antibodies against e.g. the F, SH and G protein are made. It is however impossible to discriminate between field-infected mammals and mammals vaccinated with a vaccine strain, regardless if this vaccine strain is live or inactivated, since in both cases antibodies against the virus as such will be abundantly present.

The Respiratory Syncytial virus according to the present invention surprisingly offers a solution to this problem as follows:

The SH- and G-gene are expressed in vivo in all Respiratory Syncytial virus field strains. In addition, although the SH protein is not a protein that plays a role in the induction of protective immunity against BRSV, it does induce significant amounts of anti-SH antibodies. This implicates, that mammals infected with wild-type Respiratory Syncytial virus will, next to e.g. anti-F and anti-G antibodies, always have antibodies against the SH protein. The BRSV according to the present invention however can, due to the absence of the antigenic determinants of both the SH- and the G-protein, no longer induce antibodies against those proteins. Therefore mammals vaccinated with a Respiratory Syncytial virus strain according to the invention in which the antigenic determinants of the SH- and G-protein have been deleted will not have antibodies against those proteins in their serum. In a comparative test, sera raised against the live attenuated BRSV vaccine according to the invention will therefore react with all immunogenic Respiratory Syncytial virus-proteins except for SH and G. Sera from mammals infected with an Respiratory Syncytial virus field strain however will react with all immunogenic Respiratory Syncytial virus-proteins, including SH and G. Tests based upon purified SH-, F- and G-protein directly show the presence or absence of anti-SH or anti-G antibodies. Therefore, Respiratory Syncytial viruses according to the present invention turn out to be a very suitable basis for marker vaccines, i.e. vaccines that can be serologically discriminated from a field strain. They can be discriminated by using specific diagnostic tests. Therefore still another embodiment of the invention relates to diagnostic test kits-for differentiating BRSV field-virus infected mammals from mammals vaccinated with live attenuated BRSV according to the invention. Such tests comprise the testing of serum for the absence or presence of anti-SH or anti-G antibodies.

A diagnostic test kit for the discrimination between vaccine strains and field strains can comprise e.g. a simple blocking-ELISA test in which wild-type virus is coated to the wall of a microtiter-plate. Such a plate is then incubated with serum of the animal to be tested. Subsequently, the plate is incubated with a specific and labeled antiserum against SH-protein or G-protein. If the labeled antiserum reacts with the coated virus, i.e. it is not blocked by the antiserum of the animal to be tested, this shows that that antiserum does not contain antibodies against SH- or G-protein.

Alternatively, such a diagnostic test kit can comprise an ELISA-test in which possibly purified F-, SH- or G-protein is coated to the wall of separate wells of an ELISA-plate. Incubation with serum from mammals to be tested, followed by e.g. incubation with a labeled antibody against the relevant mammalian antibody can then reveal the presence or absence of antibodies against F-, SH- or G-protein in the respective wells. Another example of a diagnostic test system is e.g. the incubation of a Western blot comprising F, SH or G protein with serum of mammals to be tested, followed by analysis of the blot.

Detection of specific anti-F-, SH- or anti-G-antibodies indicates that the tested mammal has been infected with a field strain or a vaccine strain having a single SH- or G-mutation, whereas the presence of anti-F-antibodies and lack of antibody-reaction with both the SH- and G-protein band indicates that the mammal has been vaccinated with the BRSV mutant according to the present invention.

The diagnostic test is preferably in the form of a kit, comprising the whole wild-type virus or alternatively the separate F-, SH- or G-antigens in a purified form. The antigens could e.g. be purified through standard protein separation techniques over a suitable column. Another possibility is separation on a PAGE gel followed by Western-blotting. On the Western-blot, the F-, SH- or G-protein will form a specific band, separated from other BRSV-bands, and thus is also considered to be purified. In principle, the easiest way of making such a diagnostic test system is to use purified F-, SH- or G-protein as explained above. It is however very well possible to use only part of the F-, SH- or G-protein. This with the proviso that the fragment used still comprises an antigenic determinant of F-, SH- or G-protein. All antigenic determinants of the F-, SH- or G-protein of the wild-type BRSV will induce antibodies by definition. Therefore, a truncated F-, SH- or G-protein fragment comprising even one single antigenic determinant of F-, SH- or G-protein will be capable of binding to anti-F-, anti-SH- or anti-G-antibodies.

Therefore, in another embodiment the present invention relates to a diagnostic kit for the detection of antibodies against BRSV, in which the kit comprises purified F-, SH- or G-protein or fragments thereof still comprising an antigenic determinant.

As mentioned above, the F-, SH- or G-protein can be obtained directly from cells infected with the virus particles. It is however also possible to use standard expression systems such as bacterial, yeast, baculovirus or mammalian expression systems, of which a large variety has been described in the art, for the expression of the F-, SH- or G-gene. The protein thus expressed can easily be obtained and is by definition free of other BRSV-proteins. The degree of purification is not critical. The presence of possible other proteins, such as proteins from the expression system does, since they are not F-, SH- or G-proteins, in general not disturb in diagnostic tests.

Alternatively, a diagnostic test can be used for the detection of the vaccine virus or viral antigen in the infected animal. A diagnostic test for G- and SH-free virus antigen and therefore suitable for the detection of vaccine virus according to the invention can e.g. also be a standard ELISA test, in which the wells of an ELISA plate are coated with antibodies directed against respectively the F-, the SH- and the G-protein. Viruses binding to antibodies against all three proteins are wild-type viruses, whereas vaccine viruses will only bind to the wells that comprise antibodies against the F-protein.

Therefore, another embodiment of the present invention relates to diagnostic tests comprising antibodies against respectively the F-, the SH- and the G-protein. The F-, SH- and G-protein can be used to produce such antibodies, which may be polyclonal, monospecific or monoclonal (or derivatives thereof). If polyclonal antibodies are desired, techniques for producing and processing polyclonal sera are known in the art (e.g. Mayer and Walter, eds. *Immunochemical Methods in Cell and Molecular Biology*, Academic Press, London, 1987). Monoclonal antibodies, reactive against the F, SH and G protein can be prepared by immunising inbred mice by techniques known in the art (Kohler and Milstein, *Nature*, 256, 495–497, 1975).

Still another embodiment of the present invention relates to methods for discriminating Bovine Respiratory Syncytial field-virus infected animals from animals vaccinated with the Bovine Respiratory Syncytial Virus vaccine. Such methods comprise the step of incubating a body fluid of an animal to be tested with purified F, SH and G protein or the step of incubating a tissue or a body fluid of an animal to be tested with antibodies against purified F, SH and G protein.

BRIEF DESCRIPTION OF THE FIGURES

FIG. 3: Demonstration of transcripts by Northern hybridization. Total RNA of MDBK cells infected with the indicated viruses was isolated 96 hours after infection and analyzed on a 1% agarose gel under denaturing conditions. Replicate blots were incubated with probes hybridizing to the BRSV N, SH, G, or F gene. Transcripts corresponding to the respective mRNAs and bi-cistronic mRNAs are indicated.

FIG. 4: Multi-cycle growth of rBRSV, rBRSVΔSH, rBRSVΔG, and rBRSVΔSHG in MDBK cells. Duplicate cell monolayers in 24-well dishes were infected with the indicated virus at an MOI of 0.1. Monolayers were harvested at indicated times, stored at −70° C., and titrated later in duplicate. Each value is the mean titer of material of two wells.

FIG. 6: Neutralization assay: $ND_{50}$ values for group I (mock immunized), group II (rBRSVΔG immunized group), and group III (rBRSV immunized group) up till 8 days after challenge.

EXAMPLES

Example 1

Figure 1:
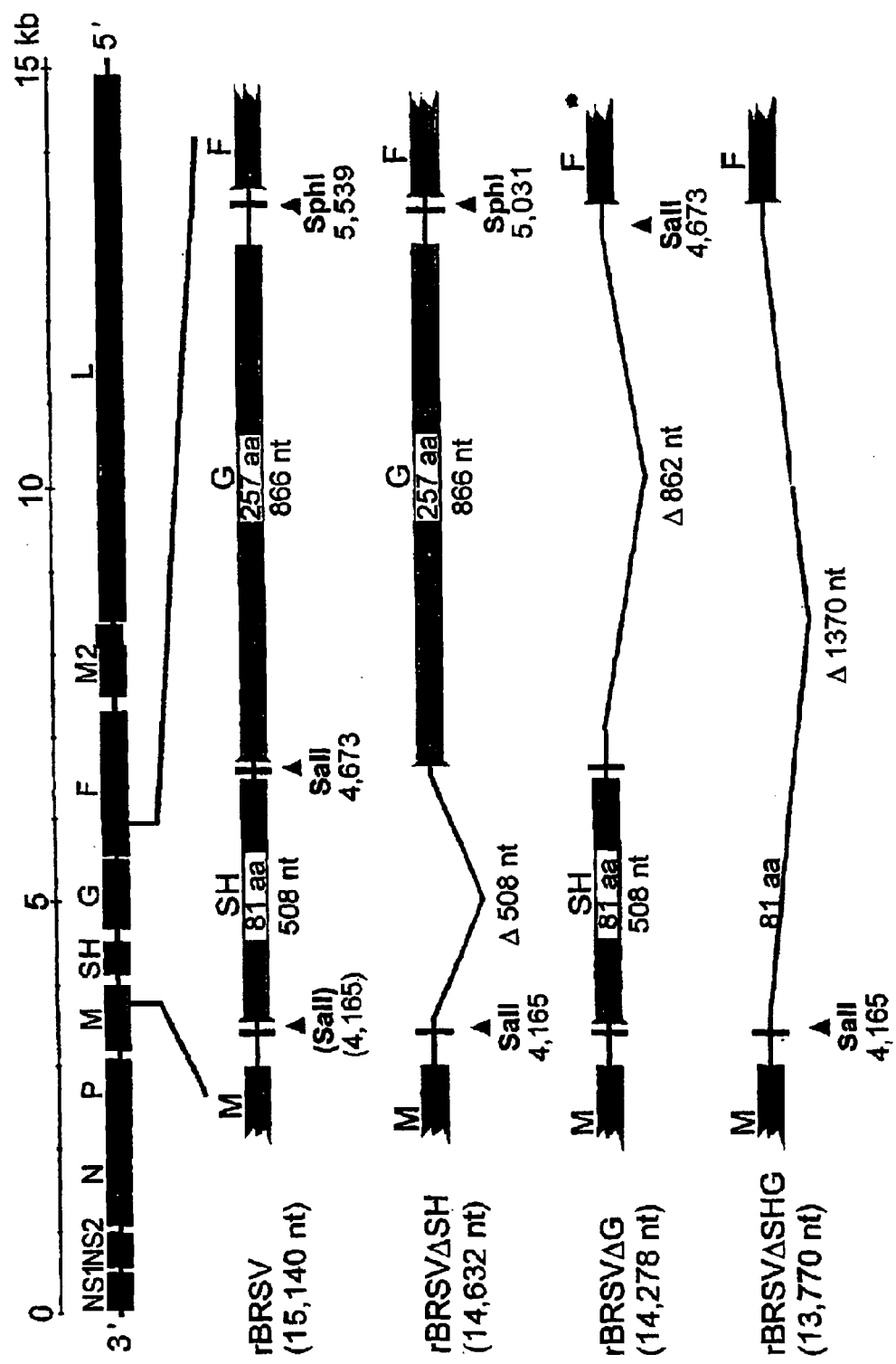
FIG. 1: Construction of BRSV protein deletion mutants. The BRSV genome is drawn to scale. The location of the ORFs are shown as shaded rectangles. The enlargements show the SH- and G-gene deletions, with the gene end signals represented by bars, and the gene start signals shown as triangles. The location of synthetic restriction sites are indicated by arrowheads. The SalI site located in the M/SH intergenic region (in parentheses) is only present in the parental plasmid used for generation of the SH- and SH/G-double-deletion mutants, and in the deletion mutants. The genome length of the recombinant viruses is indicated on the left in parentheses.

Molecular Cloning. The plasmid containing the complete antigenomic sequence of BRSV strain ATue51908 (GenBank accession no. AF 092942) as described by Buchholz, U. J., Finke, S., and K.-K. Conzelmann. (J. Virol. 73: 251–259 (1999)) was modified to contain restriction sites in the BRSV SH/G (SalI, ATue51908 nt 4673), G/F (SphI, ATue51908 nt 5539) (FIG. 1), and F/M2 (XhoI, ATue51908 nt 7471, and ClaI, ATue51908 nt 7485) intergenic regions. The SalI and SphI restriction sites were used to excise a 862 bp fragment comprising the complete BRSV G gene. After Klenow treatment and religation, the SalI site was reconstituted. In a second full length rBRSV construct, a second SalI site was created in the M/SH intergenic region (ATue51908 nt 4165). This plasmid was used to generate a BRSV SH gene deletion mutant or a double deletion mutant lacking both the BRSV SH and G gene as depicted in FIG. 1.

Generation and characterization of recombinant BRSV. Recombinant BRSVs were generated as described by Buchholz, U. J., H. Granzow, K. Schuldt, S. S. Whitehead, B. R. Murphy, and P. L. Collins. (J. Virol. 74: 1187–1199 (2000)). Briefly, 32 mm dishes of sub-confluent BHK T7/5 cells stably expressing T7 RNA polymerase were transfected with 5 μg of the respective full length plasmids (PBRSV, pBRSVΔSH, pBRSVΔG, or pBRSVΔSHG), and a set of four support plasmids (2 μg pN, 2 μg pP, 1 μg pM2 and 1 μg pL) from which the BRSV N, P, M2 and L proteins are expressed. All BRSV cDNA constructs were under control of a T7 promoter. Every two to three days, the transfected cells were split. When the cytopathic effect (cpe) was extensive, cells were frozen and thawed three times, and the clarified supernatants were used for production of virus stocks on MDBK cells as described by Buchholz et al. (2000), see above.

The identity of the recombinant viruses was verified by RT PCR. Briefly, total RNA was prepared from 32 mm dishes of MDBK cells 96 hours after infection at an MOI of 0.1. First strand cDNA was generated from 1 μg of RNA using a primer complementary to the BRSV M gene (primer Mc2b, ATue51908 nt 3612 to 3635). Second strand synthesis was done using primer Mc2b and a reverse primer BFr, hybridizing to the BRSV F gene (ATue51908, nt 5964 to 5941). The purified RT PCR product was subjected to restriction digestion and analyzed on agarose gels.

Viruses and cells. Recombinant BRSV was propagated on MDBK cells. MDBK cells were infected at an MOI of 0.1. After 90 minutes adsorption, the inoculum was removed and cells were incubated at 37° C. in MEM supplemented with 3% FCS in a 5% $CO_2$ atmosphere. At 8 days post infection, when an extensive cpe could be observed, the medium was adjusted to 100 mM $MgSO_4$ and to 50 mM HEPES (pH 7.5), and the highly cell-associated virus was released by freezing and thawing.

Growth analyses of rBRSV, rBRSVΔSH, rBRSVΔG, or RBRSVΔSHG were done on MDBK cells as described (see reference above: Buchholz et al., 2000). Titrations were carried out in duplicate in microwell plates using the limiting dilution method. To 0.1 ml of serial tenfold virus dilutions per well, $10^4$ BSR T7/5 cells were added in a 0.1 ml volume. After 48 hours, cells were fixed in 80% acetone. An indirect immunofluorescence assay using a bovine serum specific to BRSV was done and foci of infected cells were counted.

Northern Blot. Northern Blots were done as described by Buchholz, (1999) see above. Total RNA of MDBK cells infected with the recombinant viruses was analysed by denaturing agarose gel electrophoresis, blotted onto nylon membranes and UV crosslinked, and hybridized with DNA probes. Probes were generated using PCR fragments of the BRSV N (ATue51908 nt 1429 to 2277), SH (ATue51908 nt 4268 to 4534), G (ATue51908 nt 4690 to 5431), or F (ATue51908 nt 6233 to 7459) gene. They were labeled with [$P^{32}$]dCTP (3,000 Ci/mmol; ICN) (Nick translation kit, Amersham).

Results

Construction and recovery of BRSV deletion mutants. A T7 RNA polymerase driven system allowing the generation of recombinant BRSV from cDNA was used as described by Buchholz et al. (See reference to Buchholz et al., 1999 above). To generate BRSV lacking the SH, the G, or both the SH and G gene, tile full length antigenome plasmid used for recovery of recombinant BRSV was modified, resulting in deletion of regions spanning the complete SH gene or G gene, including the gene start and the gene end signals, or the SH and G gene together, from the SH gene start signal to G gene end signal. The BRSV antigenomes expressed by the respective plasmids are 14,632 nts (rBRSVΔSH), 14,278 nts (rBRSVΔG) or 13,770 nts (rBRSVΔSHG) in length, compared to 15,140 nts of the parental rBRSV (FIG. 1). Transfections were done using BSR T7/5 cells (Buchholz et al., 1999) stably expressing T7 RNA polymerase. After cotransfection of full length plasmids and a set of four support plasmids encoding BRSV N, P, L, and M2, viable recombinant BRSV was recovered from all of the cDNA constructs. About 7 days after transfection, several foci exhibiting the typical BRSV cpe of large syncytia could be observed in all transfected dishes, with no difference between the respective recombinant viruses. The deletion mutants and the parental recombinant virus were propagated by passage on MDBK cells. Five days after infection of MDBK cells at an MOI of 0.1, all virus isolates produced a comparably extensive cpe.

Figure 2:
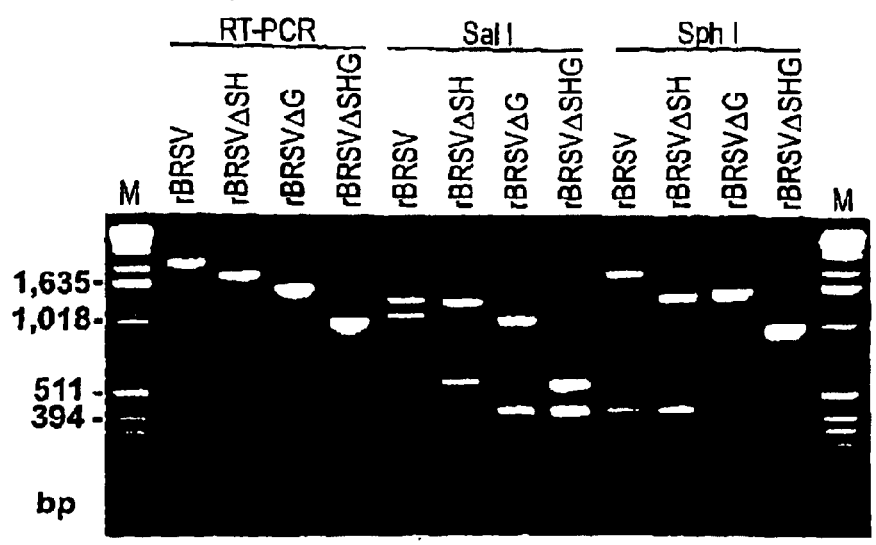
FIG. 2: Demonstration of marker restriction sites in the genomes of rBRSV and of the deletion mutants. RT-PCR was performed on total RNA of infected cells, the PCR products were subjected to restriction digestion and analyzed on a 3% agarose gel. M, 1-kb marker DNA ladder (Life Technologies) with the size of some fragments indicated. The RT-PCR products were consistent with the predicted sizes of 2,353 bp (rBRSV), 1,845 bp (rBRSVΔSH), 1,491 bp (rBRSVΔG), or 983 bp (rBRSVΔSHG). Digestion with SalI yielded the expected fragments of 1291 bp and 1062 bp (rBRSV), 1291 bp and 554 (rBRSVΔSH), 1,491 bp and 1062 bp (rBRSVΔG), or 554 bp and 429 bp (rBRSVΔSHG); digestion with SphI yielded fragments of 1928 and 425 bp (rBRSV) and 1420 and 425 bp (rBRSVΔSH). As expected, the rBRSVΔG and rBRSVΔSHG PCR fragments were not cleaved by SphI.

To verify the identity of each of the recombinant viruses, total RNA was isolated from MDBK cells 5 days after infection and processed for RT-PCR. The RT-PCR products were further analyzed by restriction digestion. As shown in FIG. 2, the RT-PCR products obtained with a primer pair hybridizing to the BRSV M gene and F gene are of the expected sizes of 2,353 bp (rBRSV), 1,845 bp (rBRSVΔSH), 1,491 bp (rBRSVΔG), or 983 bp (rBRSVΔSHG). The synthetic marker restriction sites are present in the respective RT-PCR products, as shown in FIG. 2.

Figure 3:
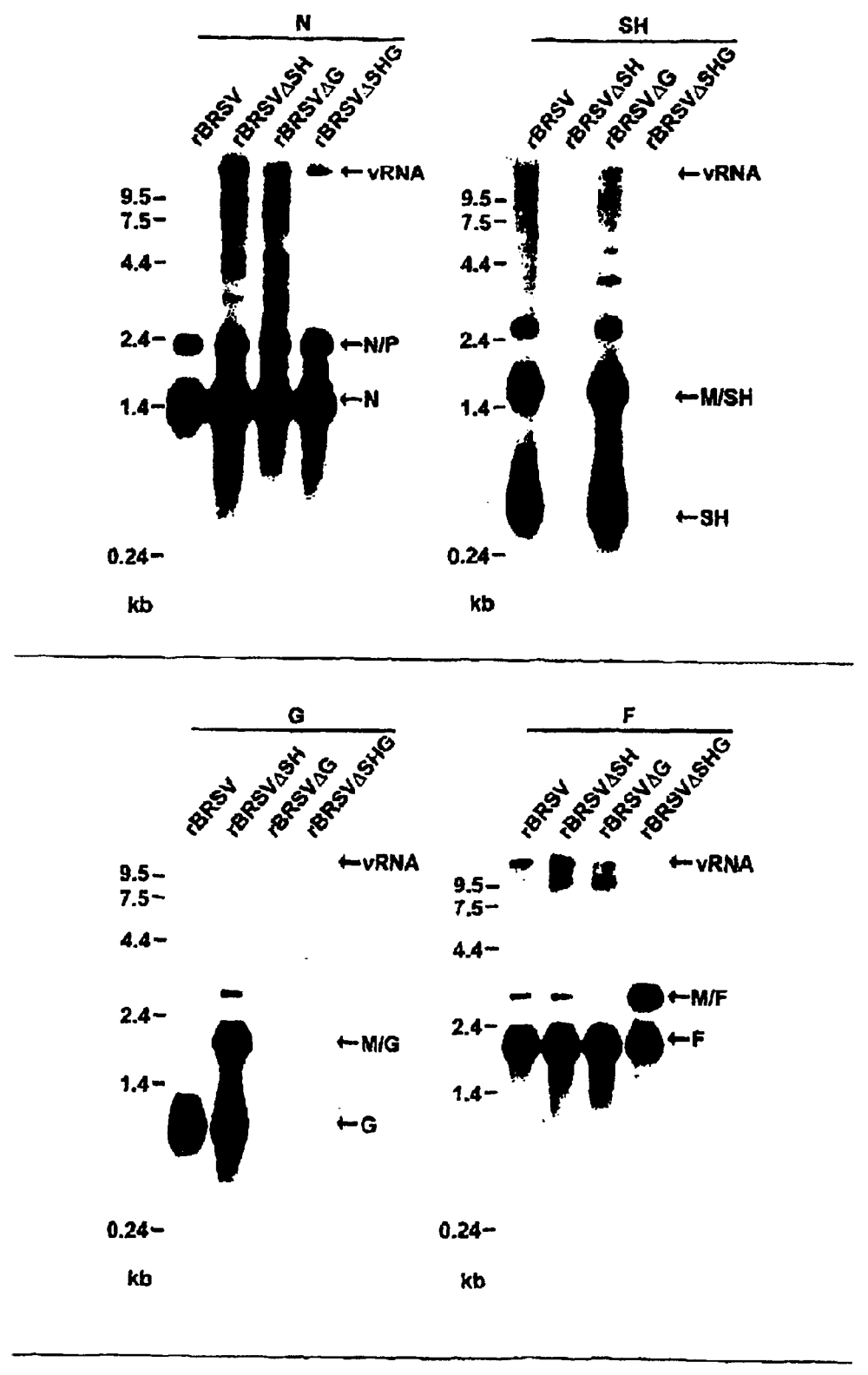

Transcription analysis of the recombinant viruses. The expression of viral RNA and of messenger RNA was verified in Northern blots performed on total RNA of infected cells (FIG. 3). The recombinant viruses exhibit a similar pattern of mRNA transcripts, differing in the absence of transcripts from the respective deleted genes. Using a probe hybridizing to the BRSV SH gene, a strong signal from bi-cistronic M/SH mRNA can be observed, with an intensity comparable to the monocistronic SH mRNA. The BRSV M gene end signal differs from the RSV gene end consensus sequence, which apparently results in an incomplete transcription termination capacity. Consequently, the deletion mutants that lack the SH or the SH and G genes are characterized by a high level of readthrough mRNAs of the M gene and the respective downstream gene. In the case of rBRSVΔSH, a probe hybridizing to the G gene yields a strong signal from bi-cistronic M/G mRNA, and the SH/G double deletion mutant yields a strong bi-cistronic M/F mRNA signal (FIG. 3).

The deletion mutants are slightly attenuated in cell culture. Growth characteristics were studied in MDBK cells. The recombinant viruses were fully viable in tissue culture with respect to multi-cycle growth competence. The growth of the BRSV deletion mutants was reduced only slightly, but reproducibly, compared to parental BRSV, see FIG. 4.

Example 2

Production of antisera. Four rabbits were immunized with 5 $\log_{10}$ PFU of rBRSV, rBRSVΔSH, rBRSVΔG, or rBRSVΔSHG in complete Freund's adjuvant. 6 weeks later, they were re-immunized with the same amount of the respective viruses in incomplete Freund's adjuvant. Sera were collected ten days later.

Indirect immunofluorescence assay. MDBK cells were infected with recombinant BRSV at an MOI of 0.1, incubated for 42 hours, fixed with 4% paraformaldehyde, and permeabilized with 1% Triton X100. Then they were incubated with monoclonal antibody (Mab) F9, directed to BRSV F, or with Mab G66, directed to BRSV G, kindly provided by Geraldine Taylor, Compton, U.K. Cells were stained with an Alexa 488 conjugated goat anti-mouse IgG (Molecular Probes, Eugene, Oreg.). The nuclei of the cells were stained with propidium iodide. Immunofluorescence was examined by confocal laserscan microscopy.

Serum neutralization. 0.05 ml of serial twofold dilutions of heat-inactivated rabbit antisera in MEM were incubated for 60 min at room temperature with an equal volume containing 2 $\log_{10}$ plaque forming units (PFU) of rBRSV. Subsequently, $10^4$ BSR T7/5 cells were added in a 0.1 ml volume. After 5 days, the $ND_{50}$ was determined. Control experiments were performed with negative sera collected prior to immunization of the rabbits.

Results

Figure 5:
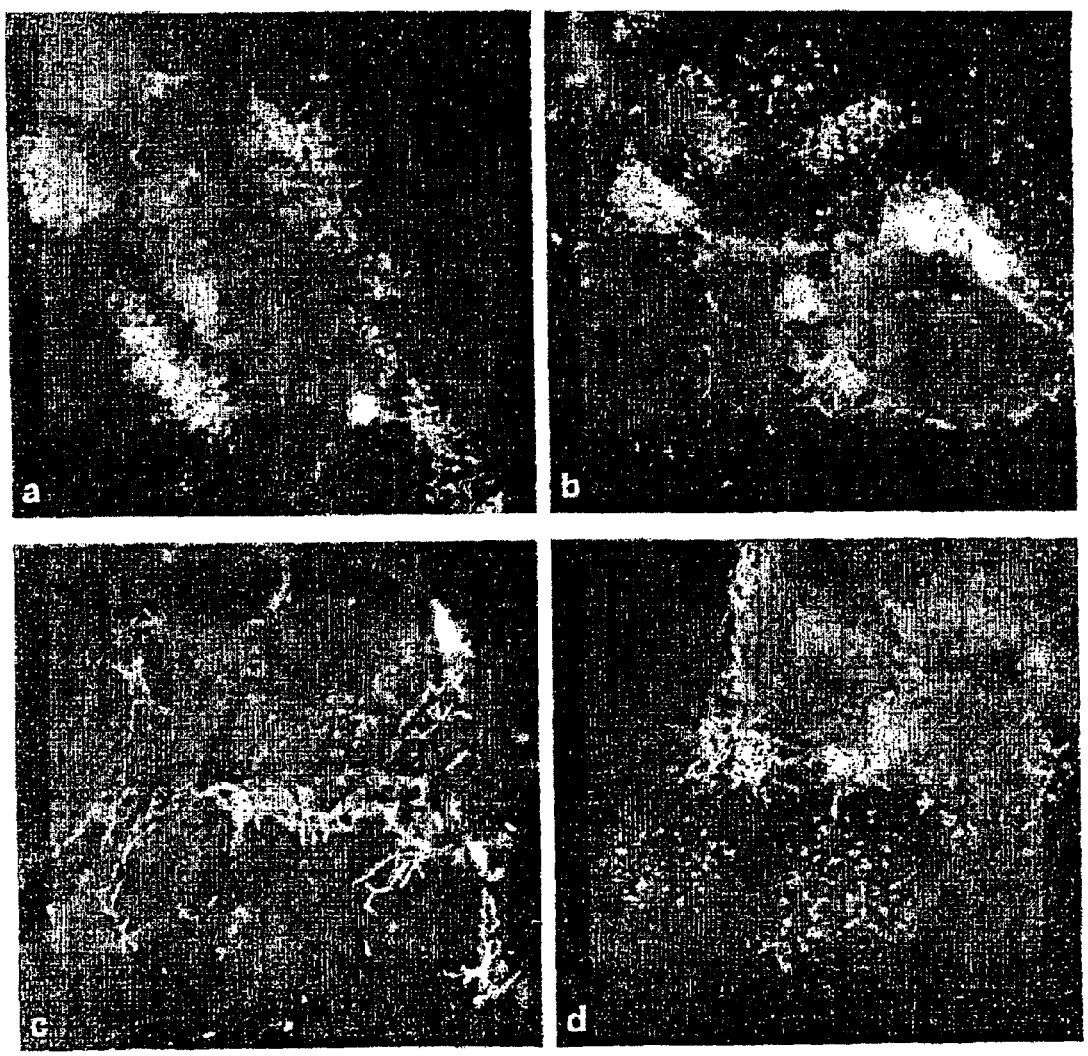
FIG. 5: Indirect immunofluorescence of MDBK cells infected with rBRSV (a), rBRSVΔSH (b), rBRSVΔG (c), or rBRSVΔSHG (d). Cells were infected at an MOI of 0.1, paraformaldehyde-fixed 42 hours post-infection, permeabilized and reacted with Mab F9, specific to the F protein of BRSV.

Expression of glycoproteins. An indirect immunofluorescence assay was performed on MDBK cells 42 hours post-infection with rBRSV or with the deletion mutants. Immunostaining with antibody F9, directed to BRSV F protein, yields a typical fluorescent staining, with infected cells surrounded by an intensely stained "corona" of long filamentous particles (FIG. 5), the deletion mutants being indistinguishable from standard rBRSV. Thus, the particle formation and incorporation of F-protein is not altered by deletion of the attachment protein or of the envelope-associated small hydrophobic protein. As expected, Mab G66 directed to BRSV G did not react with cells infected with rBRSVΔG or rBRSVΔSHG (not shown).

Antibodies induced by the deletion mutants show neutralizing activity directed to standard rBRSV. As a first test whether the deletion mutants lacking the glycoproteins SH and G were able to induce antibodies with neutralizing activity against rBRSV, antisera directed to rBRSV, rBRSVΔSH, rBRSVΔG, and rBRSVΔSHG were produced in rabbits. Sera collected after the second immunization were examined in an indirect immunofluorescence assay and in a serum neutralization assay. After the second immunization, the sera showed only weak signals in an indirect immunofluorescence test performed on Vero cells infected with rBRSV (not shown). However, all sera were able to neutralize standard rBRSV. The serum of the animal immunized with rBRSVΔSHG, lacking both SH and G genes, had an $ND_{50}$ titer against rBRSV of 32. Control sera collected from all animals prior to immunization did not confer any neutralization activity against BRSV.

Conclusion: the neutralizing antibodies induced by a recombinant BRSVΔSHG which thus carries of the envelope-associated proteins only the fusion protein F, but neither protein G nor the small hydrophobic protein SH, are capable and sufficient to neutralize wild-type BRS virus.

Example 3

Recombinant BRSV Lacking the Envelope Glycoprotein G Protect Against Challenge with Wildtype BRSV Materials and Methods Virus and cells. Recombinant bovine respiratory syncytial virus (rBRSV) (1) and rBRSV with a deletion of the glycoprotein G (rBRSVΔG) (2) were propagated on MDBK cells to obtain virus stocks for the immunization of calves. Ninety minutes after infection at an MOI of 0.1, the inoculum was removed, and cells were incubated at 37° C. in MEM supplemented with 3% FCS in a 5% $CO_2$ atmosphere. Eight days post infection, when an extensive CPE could be observed, the highly cell-associated virus was released by freezing and thawing, and cellular debris was removed by low-speed centrifugation. Material for mock-immunization of calves was prepared from uninfected MDBK cells which were treated identically.

Experimental design, challenge model. Eleven conventionally reared calves were obtained from a local dairy herd. The calves were colostrum-fed and taken to the isolation facilities when they were between two and eight days of age. After the transport, seven calves showed mucopurulent nasal discharge and *Pasteurella multocida* was isolated from the nasal swabs. In order to prevent pneumonia, all calves received a singular antibiotic treatment. The calves were fed milk-replacer, hay pellets and grain flakes. The calves were shown to be free from BRSV, BVDV, IBR and BPIV-3. However, three calves had low maternal antibody titers against BRSV, with neutralizating titres of 2 log2.

At the age of two months, the calves were alloted to three groups. Group I (mock vaccination) consisted of three calves, groups II (vaccination with rBRSVΔG) and group III (vaccination with or rBRSV) consisted of four calves each. Each of the three seropositive calves was assigned to one of the groups, and the seronegative calves were allotted at random. In group I, each calf received a mock vaccination consisting of 8 ml of MDBK cell culture suspension which was applied intranasally. Animals of group II were vaccinated intranasally with the same volume, containing $8 \times 10^6$ PFU of rBRSVΔG. Calves of group III were vaccinated intranasally with $8 \times 10^6$ PFU of rBRSV. After immunization, clinical assessments (body temperature, heart rate, breathing rate, coughing and abnormal lung sounds, nasal or ocular discharge, depression) were made daily for ten days and nasal swabs were taken daily. After ten days, the clinical examinations were done twice a week and nasal swabs were taken weekly. On day eight, 15, 29 and 35, blood samples were taken.

Six weeks after immunization, the calves were challenged with low-passaged wild-type BRSV, strain CA-1 (a generous gift from Laurel Gershwin, Davis, Calif.), via aerosol. The virus suspension ($5 \times 10^4$ PFU in a 10 ml volume per calf) was aerosolized by an ultrasonic nebulizer (Nebutur 310, TUR Elektromedizin, Hohen Neuendorf), and admitted to the calves using a flexible tube and a face mask. After the challenge, clinical examinations, as described above, and nasal swabs were carried out daily. Blood samples were taken on day eight after challenge. On day eight after the challenge, the calves were necropsied.

Pathological examination. The relative size of pneumonic lung area was estimated for each lobe and recorded on a standard lung diagram. Lesions up to 1% of the whole lung were denoted as (+), + marked a range between 1% and 10%, ++ between 11% and 20%, +++ between 21% and 50%, and ++++ designated pneumonic lesions exceeding 50% of the lung. The lobes used for tissue sampling were clamped off and a tracheobronchial lung wash was done. Tissue samples were taken for virological, histological and bacteriological examinations. In addition, tissue samples were fixed and processed for histological (H. E.) staining and for immunohistological characterizations using a monoclonal antibody specific for the BRSV F protein.

Virus isolation. Recovery of BRSV was done from nasal swabs, and post-mortem from tracheobronchial lavage fluid, lung lobes, and from Lnn. mediastinales. The nasal swabs were collected in 2 ml of MEM. The lavage fluid was centrifuged and the supernatant was used for virus isolation. The tissue samples and the lymphnodes were homogenized in Hank's medium containing sucrose (0,218 M) and antibiotics in a mortar, yielding a 20% tissue suspension.

After a 1 h incubation at room temperature, the suspensions were frozen and thawed once. Debris was removed by low-speed centriugation. Kop-R cells (Kop-R, CCLVRIE244, a permanent cell line generated from oesopharyngeal tissue of a newborn calf, obtained from Roland Riebe, Insel Riems) were used for virus isolation. Monolayers of Kop-R cells were incubated with serial tenfold dilutions of lavage fluid, nasal swabs, or of tissue homogenisate supernatant. After 2 hours adsorption, the inoculum was removed, the monolayer was washed once, and incubated for seven days. All cell cultures were performed whit antibiotics added to the cell culture medium. In case of CPE, the cells were acetone fixed, and tested for BRSV in an indirect immunofluorescent assay, using a polyclonal rabbit hyperimmuneserum specific for the BRSV matrix protein. If no CPE was detectable, the cell cultures were passaged three times in 7 day-intervalls. Finally, an indirect immunofluorescent assay was done to confirm negative results.

Neutralization assay. The sera were heat inactivated, and incubated in serial twofold dilutions with an equal volume of rBRSV, containing 100 $TCID_{50}$ of BRSV per 50 μl, for one hour at room temperature. Subsequently, $10^4$ BSR T7/5 cells were added in a 0.1 ml volume. After four days, the $ND_{50}$ was determined as the reciprocal serum dilution resulting in inhibition of CPE in half of the parallel wells.

Indirect immunofluorescence assay. BSR T7/5 cells (1) were transiently transfected with expression plasmids which contain the open reading frames of the BRSV G or F protein, respectively, under control of the T7 RNA polymerase promoter. Two hours post transfection the cells were split and seeded into a microtiter plate. 24 hours post transfection the cells were acetone-fixed and incubated with heat inactivated calf sera diluted 1:100 in PBS and subsequently stained with FITC-conjugated goat anti-bovine IgG secondary antibody. Monoclonal antibodies specific for BRSV G or F protein served as controls.

Results

Clinical signs. After intranasal immunization, no clinical signs were observed in any of the groups, with the exception of one calf of the rBRSV group which rarely showed slight coughing (Table 1).

After the challenge, the calves of the mock-immunized group showed mild to severe clinical disease (Table 1). Two calves had only a slight raise in body temperature, accompanied by mild coughing. One animal suffered from serious respiratory distress. The rectal temperature was increased, and the respiratory rate was more than twofold increased. Frequent spontaneous coughing and abnormal lung sounds were observed. This calf was euthanized on day 7 because of heavy respiratory distress. The calves of the rBRSVΔG group showed post-challenge only mild coughing, and for three out of four animals a slight raise of rectal temperatures was observed. In the rBRSV group, only one calf showed an increase in rectal temperature, and rare coughing was seen in two calves (Table 1).

Virus isolation. After immunization with rBRSV, virus could be reisolated from nasal swabs from day 2 until day 8 (Table 2). The virus titers of the nasal swab samples were ranging between 1.0 log 10 and 4.1 $log_{10}$ PFU per ml. After immunization with rBRSVΔG, virus recovery from nasal swabs was unsuccessful, even after the third passage. As expected, after mock-immunization, no virus could be isolated from nasal swabs.

After the challenge, in the mock-immunized group virus was recovered from nasal swabs from day 3 up to day 7 from all calves, with titers from 1.6 $log_{10}$ to 3.4 $log_{10}$ per ml. In the vaccinated groups, at least one passage of cells inoculated with nasal swab material was necessary to detect virus replication, with the exception of calf 41 of the rBRSVΔG-group, showing low nasal swab titres of up to 1.6 log10, detected on three consecutive days (Table 2).

Serology. After intranasal vaccination, the sera obtained from the calves of the rBRSV and the rBRSVΔG groups showed an increase in neutralizing activity (FIG. 1). In detail, in the group immunized with rBRSV, the $ND_{50}$ titers increased up to values between 32 and 256, with an increase resembling that occuring after natural infections. The $ND_{50}$ titers of the rBRSVΔG-group stayed on a moderate level of 8 to 24 until day 35 after vaccination. Prior to challenge, none of the calves of the mock-immunized group had neutralizing antibody titers ($ND_{50}$) against BRSV higher than 4.

After challenge, the animals in the rBRSVΔG-group showed a four- to sixfold increase in the $ND_{50}$ eight days after BRSV exposure, whereas in the rBRSV group, a slight increase in neutralizing activity was found only in one out of four calves (FIG. 6).

To further characterize the serological response with respect to its specificity for BRSV G and F, an indirect immunofluorescence test was performed on BSR T7/5 cells, 24 hours after transfection with expression plasmids for the BRSV G or F proteins, respectively. In the group immunized with rBRSV, antibodies to BRSV G and F were detected on day 35 after immunization, with no increase of fluorescence signal 8 days after challenge (Table 3). In the mock-immunized group, antibodies of the IgG subclass could not be detected 8 days after challenge, neither against BRSV G nor against F. As expected, the calves immunized with rBRSV☐G did not develop antibodies specific for BRSV G. However, in contrast to animals of the mock-immunized group, all of the animals of the rBRSVΔG group did develop a detectable level of IgG antibodies specific for BRSV F, eight days after challenge (Table 3). Taken together, the post-challenge serological reaction of the animals immunized with rBRSV☐G can be taken as evidence of a prior priming effect by rBRSVΔG.

Pathological findings. In the mock-immunized group, the relative amount of atelectatic lung area was higher than the amount found in the rBRSVΔG group and in the group vaccinated with rBRSV (Table 4). Evaluation of these data has to include the histopathological findings. Whilst in the atelectatic areas in the rBRSVΔG group only chronic lesions without syncytial cells were present, the changes in the mock-immunized group were characterized as acute pneumonic lesions. Moreover, in the lung of calf 26, which had shown the most severe clinical disease and had been necropsied an day 7 after challenge, syncytial cells were found. These results were confirmed by the immunohistological findings. In two out of three calves of the mock-immunized group, the indirect immunofluorescence assay revealed large areas of alveolar epitheliar cells showing BRSV specific immunofluorescence. These areas were present in several lung lobes, whereas in the vaccinated groups only few specifically stained single cells could be observed.

References

1. Buchholz, U. J., Finke, S., and K.-K. Conzelmann. 1999. Generation of bovine respiratory syncytial virus (BRSV) from cDNA: BRSV NS2 is not essential for virus replication in tissue culture, and the human RSV leader region acts as a functional BRSV genome promoter. J. Virol. 73: 251–259.
2. Karger, A., U. Schmidt, and U. J. Buchholz. 2001. Recombinant bovine respiratory syncytial virus with deletions of the G or SH genes: G and F proteins bind heparin. J. Gen. Virol. 82:631–640.
3. Taylor, G., E. J. Stoft, J. Furze, J. Ford, and P. Sopp. 1992. Protective epitopes on the fusion protein of respiratory syncytial virus recognized by murine and bovine monoclonal antibodies. J. Gen. Virol. 73:217–2223.

TABLE 1

Clinical signs post-challenge

| | | | Day post-challenge | | |
|---|---|---|---|---|---|
| Virus | Calf | Fever[a] | Respiration rate[b] | Lung sounds | Cough[c] |
| mock | 26 | 5, 6, 7 | 5, 6, 7 | 6, 7 | + 5, ++ 6, 7 |
| | 36 | | | | (+) 6 |
| | 37 | | | 3, 4, 5, 6, 7, 8 | (+) 6, 7 |
| rBRSVΔG | 28 | | | | (+) 3, 4, 5, 7 |
| | 41 | | | | (+) 5, 7 |
| | 76 | 5, 7 | | | (+) 3, 4, 5, 6, 7 |
| | 77 | | | | (+) 3, 4, 7 |
| rBRSV | 29 | | | | |
| | 35 | | | | (+) 6 |
| | 74 | | | | (+) 1 |
| | 79 | 5 | | | |

[a]body temperature exceeding the mean value 1° C. or more
[b]respiration rate greater than the baseline mean value plus twice the standart deviation of the baseline mean
[c](+), mild cough, rarely seen, +, more frequent, ++ frequent cough

TABLE 2

Replication of rBRSV, rBRSVΔG, and CA-1 in the upper respiratory tract of calves

| | | Nasal swab titer (log$_{10}$ pfu/ml) | | | | | | | | | | | | | | | | | |
|---|---|---|---|---|---|---|---|---|---|---|---|---|---|---|---|---|---|---|---|
| | | Day post-inoculation | | | | | | | | | | Day post-challenge | | | | | | | |
| Virus | Calf | 1 | 2 | 3 | 4 | 5 | 6 | 7 | 8 | 9 | 10 | 1 | 2 | 3 | 4 | 5 | 6 | 7 | 8 |
| mock | 26 | | | | | | | | | | | | | | | | | | |
| | 36 | | | | | | | | | | | | | | | | | | |
| | 37 | | | | | | | | | | | | | | | | | | |
| rBRSVΔG | 28 | | | | | | | | | | | | | | | | | | 2$^{nda}$ |
| | 41 | | | | | | | | | | | | | | | | | | 1$^{st}$ |
| | 76 | | | | | | | | | | | | | | | | | | 1$^{st}$ |
| | 77 | | | | | | | | | | | | | | | | 1$^{st}$ | 1$^{st}$ | 1$^{st}$ |
| rBRSV | 29 | | | | | | | 1$^{st}$ | | | | | | 1$^{st}$ | | | | | |
| | 35 | | | | | | | | | | | | | 1$^{st}$ | | 1$^{st}$ | | | |
| | 74 | | | | | | | | 2$^{nd}$ | | | | | | | | | | |
| | 79 | | | | | | | | | | | | | | | | | | |

[a]italics: virus detection in passage number

TABLE 3

Antibodies directed against BRSV G and F

| Virus | Calf no. | F 0[b] | F 35[c] | F 7/8[d] | G 0 | G 35 | G 7/8 |
|---|---|---|---|---|---|---|---|
| mock | 26 | − | − | − | − | − | − |
|  | 36 | − | − | − | − | − | − |
|  | 37 | − | − | − | − | − | − |
| rBRSVΔG | 28 | − | − | + | − | − | − |
|  | 41 | − | − | + | − | − | − |
|  | 76 | − | − | + | − | − | − |
|  | 77 | − | − | + | − | − | − |
| rBRSV | 29 | − | + | + | − | + | + |
|  | 35 | − | + | + | − | + | + |
|  | 74 | − | + | + | − | + | + |
|  | 79 | − | + | + | − | + | + |

[a]calf sera tested in an indirect immunofluorescence assay (IFA) on cells transiently transfected with BRSV G or F
[b]before immunization
[c]day 35 after immunization
[d]day 7/8 after challenge

TABLE 4

Pathological and histological examinations

| Virus | Calf | Pneumonic lesions | Histopathological findings | Lung lobe[b] | IFA |
|---|---|---|---|---|---|
| mock | 26 | ++++[a] |  | 3 |  |
|  |  |  |  | 5 |  |
|  |  |  |  | 7 |  |
|  | 36 | + | chronic[c] | 2 | − |
|  |  |  |  | 5 | − |
|  |  |  |  | 6 | − |
|  | 37 | ++ |  | 2 |  |
|  |  |  |  | 3 |  |
|  |  |  |  | 4 |  |
| rBRSVΔG | 28 | (+) |  | 3 | − |
|  | 41 | ++ | chronic | 2 | − |
|  | 76 | ++ | chronic | 3 | − |
|  |  |  |  | 4 | − |
|  | 77 | − |  | 2 | (+) |
|  |  |  |  | 3 | − |
| rBRSV | 29 |  |  | 1 | − |
|  |  |  |  | 2 | − |
|  |  |  |  | 3 | − |
|  | 35 | (+) |  | 2 | − |
|  |  |  |  | 4 | − |
|  |  |  |  | 5 | − |
|  | 74 | (+) |  | 2 | (+) |
|  |  |  |  | 3 | − |
|  | 79 | − |  | 2 | − |
|  |  |  |  | 3 | − |

[a]Pneumonic lung area: (+) less than 1%, + 1 to 10%, ++ 11 to 20%, +++ 21 to 50%, ++++ more than 50%.
[b]Lung lobes: 1, left apical cran., 2, left apical caud., 3, left diaphragmaticus, 4, right apical cran., 5, right apical caud., 6, medius, 7, right diaphragmaticus.
[c]Chronic-atelectatic lesions.

We claim:

1. A Bovine Respiratory Syncytial Virus incapable of expressing a functional G-protein due to a mutation in the gene encoding said protein.

2. A vaccine for the protection of cattle against BRSV-infection, comprising:

a Bovine Respiratory Syncytial virus according to in claim 1 and a pharmaceutically acceptable carrier.

3. The vaccine according to claim 2, further comprises an adjuvant.

4. Vaccine according to claim 2, wherein said vaccine is in a freeze-dried form.

5. A method for the preparation of a vaccine for the protection of cattle against Bovine Respiratory Syncytial Virus infection, comprising:

admixing the Bovine Respiratory Syncytial Virus according to claim 1 and a pharmaceutically acceptable carrier.

6. An immunogenic composition, comprising:

the Bovine Respiratory Syncytial virus according to claim 1.

* * * * *